United States Patent [19]
Merritt, Jr.

[11] Patent Number: 5,803,736
[45] Date of Patent: Sep. 8, 1998

[54] DENTAL CAST POST FOR DIRECT INTRAORAL PATTERNS

[76] Inventor: Kenneth L. Merritt, Jr., 406 Estate Dr., Hendersonville, N.C. 28739

[21] Appl. No.: 232,987

[22] Filed: Apr. 25, 1994

[51] Int. Cl.[6] ................................................ A61C 05/08
[52] U.S. Cl. ........................ 433/213; 433/220; 433/224
[58] Field of Search ................................ 433/102, 213, 433/218, 224, 214, 220, 221, 225

[56] References Cited

U.S. PATENT DOCUMENTS

| D. 273,984 | 5/1984 | Vlock . | |
|---|---|---|---|
| 4,483,678 | 11/1984 | Nishro et al. | 433/201 |
| 4,536,158 | 8/1985 | Bruins et al. | 433/201.1 |
| 4,600,392 | 7/1986 | Weissman | 433/225 |
| 4,684,555 | 8/1987 | Neumeyer | 428/36 |
| 4,934,936 | 6/1990 | Miller | 433/220 |
| 4,952,150 | 8/1990 | Schiwiora et al. | 433/220 |
| 5,112,225 | 5/1992 | Diesso | 433/48 |
| 5,275,562 | 1/1994 | McSpadden | 433/224 |
| 5,302,129 | 4/1994 | Heath et al. | 433/224 |
| 5,382,161 | 1/1995 | Roane | 433/224 |

*Primary Examiner*—Stephen Funk
*Assistant Examiner*—Steven S. Kelley
*Attorney, Agent, or Firm*—Joseph T. Guy, Jr.

[57] ABSTRACT

An improved dental post is provided in an apparatus for forming a pattern of an apical canal comprising:
 an elongated apical shaft;
 a transfer head axially attached to one end of the apical shaft; and
 a thermoplastic encasing the apical shaft.

17 Claims, 1 Drawing Sheet

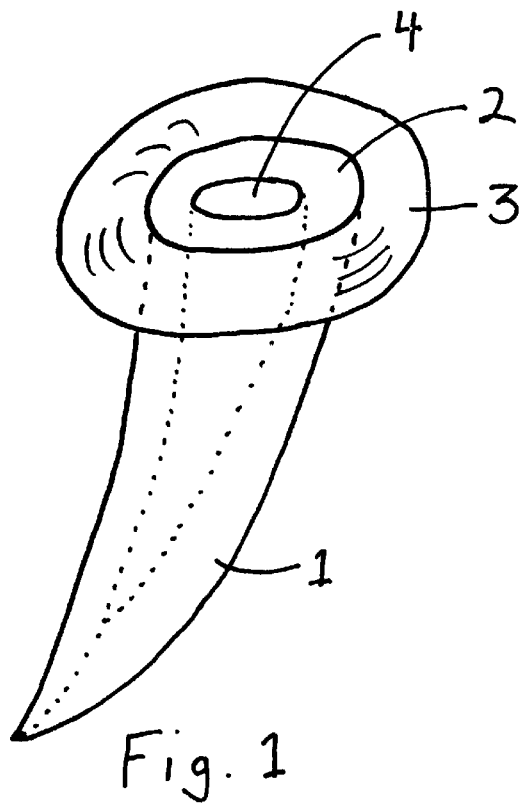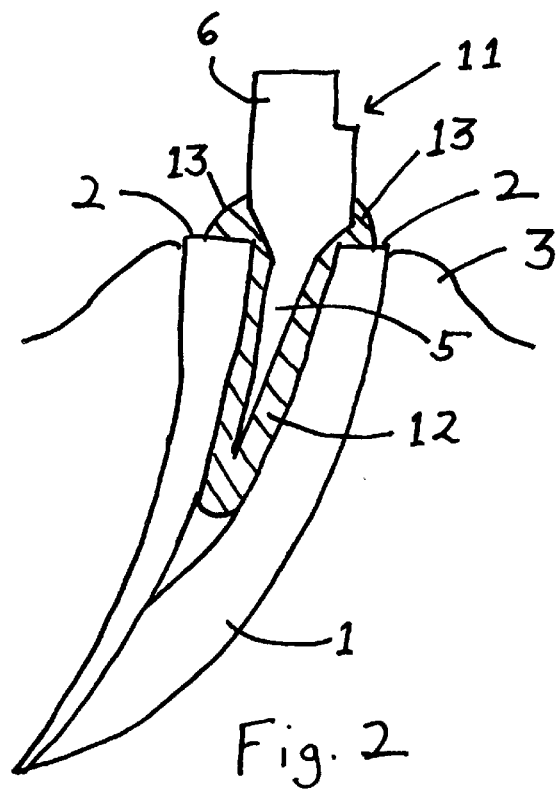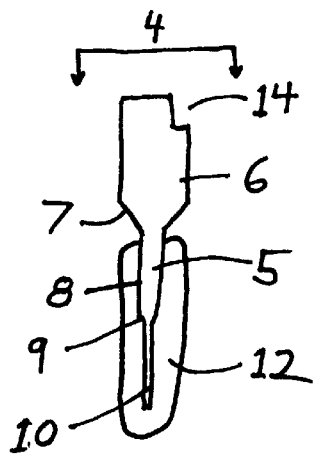

DENTAL CAST POST FOR DIRECT INTRAORAL PATTERNS

BACKGROUND OF THE INVENTION

This invention relates generally to an improved method for obtaining a pattern for a dental cast post.

The use of dental post for restoration of a superstructure onto a tooth stub is well known. Typically, the tooth stub is prepared from a damaged tooth by cutting down to the undamaged portion of the tooth. The apical canal is then prepared and a dental post is cemented therein.

A post is usually either prefabricated or custom cast. With a prefabricated post a core for retaining the crown is built around the upper portion of the post after cementation. With a cast post, the core is generally cast as a part of the post and is then cemented as one unit. In addition, cast posts are generally of two varieties. One variety utilizes a prefabricated post pattern, usually plastic, to which tooth structure is drilled away until the plastic pattern fits into the tooth. This type of post involves fitting the tooth to a prefabricated post pattern. It can result in sacrificing excess tooth structure so as to achieve a favorable relationship between the post and apical canal. The second variety of cast post involves generating a custom post pattern which intimately resembles the internal shape of the apical canal. This custom post pattern is then replicated into a metal casting which is cemented into the tooth. This invention relates to an improved method for preparation of a custom cast post pattern. Previous methods for generating a post pattern involve mixing various materials together, such as monomers and polymers, and flowing this material down into the canal. In addition, a core pattern fabrication was required followed by casting and cementing of the post prior to forming the impression for the final restoration. Due to the chemical nature of these patterns they are slow setting and the patterns formed are of low density which leads to a rough casting which requires surfacing.

Various prefabricated dental post are available to the practitioner including post with threads or fluted designs as detailed in U.S. Pat. Nos. D273,984; 4,483,678; 4,684,555 and 4,934,936. Dental post comprising ribs are detailed in U.S. Pat. No. 4,600,392. All of these dental post suffer from at least one of several deficiencies.

One deficiency with prior art dental post is an inaccurate match between the shape of the apical canal and the dental post. The inaccurate match creates voids between the apical canal and the dental post which must be filled with dental cement to insure a tight setting. Ribs also improve the fit yet they typically require drilling to insure an accurate fit. Any drilling may decrease the integrity of the tooth and is therefore to be avoided if at all possible. Conventional prefabricated dental post also involve the step of core formation after the dental post is inserted.

There has been a long felt need in the art to provide a dental post with a custom fit external contour which accurately matches the interior contour of the apical canal.

SUMMARY OF THE INVENTION

It is an object of the present invention to provide a dental post which rapidly and accurately conforms to the shape of the internal anatomy of the tooth root.

It is another object of the present invention to provide a dental post which can be applied with minimal drilling of the tooth.

It is another object of the present invention to provide a dental post with a transfer head which eliminates the necessity of chairside core pattern fabrication.

It is yet another object of the present invention to provide a dental post which can be custom fit to the apical canal.

It is yet another object of the present invention to provide a dental post which does not require altering the shape of the apical canal to conform to the shape of the dental post.

These and other advantages are provided in an apparatus for forming a pattern of an apical canal comprising:
an elongated apical shaft;
a transfer head axially attached to one end of said apical shaft;
a thermoplastic encasing said apical shaft.

Particularly preferred embodiments of the present invention are obtained with a thermoplastic comprising a caprolactone defined by the formula:

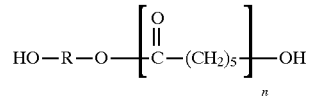

wherein R is an aliphatic hydrocarbon of 1 to about 25 carbons and n is an integer of 300 to 650.

A particularly preferred embodiment is provided in a process for forming a cast post dental restoration pattern comprising the steps of:
(a) inserting a dental post blank into the apical canal wherein said dental post blank comprises:
(i) an elongated apical shaft;
(ii) a transfer head axially attached to said apical shaft;
(iii) a viscous thermoplastic encasing said apical shaft;
(b) allowing said viscous thermoplastic to harden thereby forming a rigid impression of said apical canal.

Particularly preferred embodiments include the additional process of either constructing a dental restoration pattern on said transfer head, or forming a core, or forming a cast and molding a replicate.

BRIEF DESCRIPTION OF DRAWINGS

FIG. 1 is a perspective view of a tooth stub.

FIG. 2 is a cross-sectional view of the present invention inserted into the apical canal of a tooth.

FIG. 3 is a view of the operative dental post of the present invention.

FIGS. 4a–4d are top views of different embodiments of the transfer head of the present invention.

DETAILED DESCRIPTION OF THE INVENTION

Throughout the following description similar elements are numbered accordingly.

FIG. 1 is a perspective view of a tooth stub which has been previously prepared as known in the art. The tooth stub, 1, terminates at the prepared upper surface, 2, in the vicinity of the gum, 3. The apical canal, 4, will receive the dental post of the present invention.

The term "apical canal" refers to both the actual apical canal present in a tooth and to a replicate thereof as typically available when indirect cast post are prepared. Similar voids outside the field of dentistry may be modeled using the invention as will be apparent from the description.

FIG. 2 is a dental post blank of the present invention inserted into the apical canal of a tooth, 1, in accordance with the present invention. FIG. 3 is a view of the dental post blank of the present invention prior to insertion into an apical canal. The apical shaft, 5, of the dental post blank, 11, is encased in thermoplastic, 12, which substantially fills the apical canal. A sufficient amount of thermoplastic is used such that when inserted into the apical canal a bead, 13, of thermoplastic is formed on the upper surface, 2, of the tooth, 1, without overflowing onto the gum, 3. Some important elements of the bead are covering the optional bevel, 7, of the dental post blank, 11, to insure that recesses are not present; clearing the marginal areas; and the size of the bead should be smaller than any anticipated core. The thermoplastic, 12, and dental post blank, 11, are inserted into the apical canal when the thermoplastic is viscous. The thermoplastic fills the apical canal and is allowed to harden thereby insuring a rigid impression of the apical canal. The dental post blank, 11, comprises an apical shaft, 5, for inserting into the apical canal and a transfer head, 6. The transfer head is typically larger than the apical shaft and with this configuration they are joined at a bevel, 7. The apical shaft, 5, is a slender, substantially round, rod-like structure capable of loosely fitting within an apical canal of a tooth. The apical shaft may be continuously tapered as shown in FIG. 2 or it may consist of first section, 8, with a first diameter, a transitional neckdown, 9, and a second section, 10, with a second diameter which is smaller than the first diameter. A multiplicity of sections may be so described as may a combination with tapered sections. The dental post blank is preferably manufactured from plastic such as polyalkylene, preferably polyethylene or polypropylene, polycarbonate, and the like. The transfer head may be the same size as the apical shaft but preferably the transfer head is larger in diameter than the apical shaft. Preferably the transfer head is about 1 mm to 3 mm in width. The transfer head is preferably 3 mm to 10 mm in length. Below about 3 mm the transfer head is to small for practical use and above 10 mm the transfer head may interfere with subsequent operations. Preferably, the transfer head is about 5 mm to about 7 mm in length. The apical shaft is preferably about 4 mm to about 18 mm in length and more preferably about 8 mm to about 14 mm in length. Most preferably the apical shaft is about 12 mm in length. The diameter of the apical shaft is preferably about 0.4 mm to about 1.3 mm and most preferably about 1 mm near the transfer head and about 0.7 mm on the end away from the transfer head.

The transfer head, 6, may act as a handle for removing the dental post blank after the thermoplastic is rigid. This is typically useful when a core may be prepared as on a conventional post. The transfer head may also act in a manner similar to a core wherein a crown is prepared directly over the transfer head. In this embodiment it is preferable that the transfer head comprises a registration notch, 14, which when surrounded by dental impression material insures that the proper orientation between the crown, or superstructure, and the apical canal is maintained throughout the casting process. The registration notch shape is preferably rotationally asymmetrical such that only one rotational orientation of transfer head and superstructure will fit. Examples of particularly preferred transfer heads illustrated in FIGS. 4a–4d include trapezoids, semi-circles, and the like, or the transfer head may have protrusions or depressions such as slots, grooves, ribs and the like. The interior of a superstructure formed on the transfer head will be keyed to the transfer head.

Thermoplastic is specifically chosen to have a crystal melting point which is low enough to not cause thermal damage to the tooth or surrounding tissue and yet still be frozen at standard intraoral temperatures. Preferably, the thermoplastic has a crystal melting point of approximately 120° to 160° F. which is easily within the range of the water obtained from most commercial and residential hot water heaters. It is also preferable that the thermoplastic be rigid at approximately 105° F. or thereabouts to insure that the shape of the apical canal is maintained with minimal risk of melting extraorally. It is also preferable that the thermoplastic does not shrink over the operating temperature range since shrinkage would cause the thermoplastic to pull away from the wall of the apical canal.

A preferred thermoplastic for use in the present invention comprises at least 75%, by weight, of a polycaprolactone of the formula:

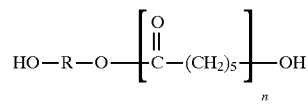

wherein R is an aliphatic hydrocarbon of 1 to about 25 carbons and n is an integer of 300 to 650.

The preferred average molecular weight of the polycaprolactone is from about 35,000 to about 60,000. The most preferred caprolactone polymer is a mixture of 35 parts by volume of TONE P-700 and 65 parts by volume of TONE P-767. Both of these polymers are manufactured by Union Carbide Corporation, U.S.A. The preferred form is extruded rods although beads and pellets are available.

TONE P-700 and TONE P-767 are described as homopolymers of ε-caprolactone. The polymerization is initiated by a diol (HO—R—OH). The caprolactone is a seven-membered ring. TONE P-767 has an average molecular weight of approximately 43,000 and is prepared from a special high purity grade of caprolactone monomer. Typical properties of TONE P-767 are a tensile strength psi (MPa) of 3000–4500 (21.0–31.0) and elongation % of 600–1000; and a melting point (by DSC) of 55°–65° C.

TONE P-700 is semi-rigid at room temperature. The basic physical properties are shown in Table 1.

TABLE 1

| | |
|---|---|
| Tensile Modulus, psi (MPa) | 60,000 (414) |
| Yield Stress, psi (MPa) | 1600 (11.0) |
| Tensile Strength, psi (MPa) | |
| 2 in/min | 4,500 (31.0) |
| 20 in/min | 4,000 (27.6) |
| Ultimate Elongation, % | |
| 2 in/min | 600 to 800 |
| 20 in/min | 600 to 800 |
| Flexural Modulus, psi (MPa) | 62,000 (428) |
| Flexural Stress at 5% strain, psi (MPa) | 2,470 (17.1) |
| Notched Izod Impact Strength, 1/2 inch bar ft-lb/in of notch (J/m) | 3 to 8 (160 to 425) |
| Unnotched Izod impact Strength 1/2 inch bar | No Break |
| Tensile Impact Strength, ft-lb/in (KJ/M) | 60 (126) |
| Density, p g/cc at | |
| 0° C. | 1.160 |
| 20° C. | 1.149 |
| 40° C. | 1.134 |
| 60° C. | 1.070 |
| 90° C. | 1.050 |
| Δp/ΔT at −30° C. to 30° C. g/(cc °C.) | −5.6 × 10$^{-4}$ |
| Δp/ΔT at 60° C. to 100° C. g/(cc °C.) | −6.8 × 10$^{-4}$ |
| Moisture Content | |
| at 50% Relative Humidity, % | 0.07 |
| at 100% Relative Humidity; % | 0.43 |

Thermal properties of TONE P-700 are given in Table 2. The crystalline melting point is about 140° C.

TABLE 2

| | |
|---|---|
| $T_m$ Crystalline Melting Point[1], °C. | 60 |
| Tg Amorphous, °C. | −70 |
| Tg, Partialty Crystalline, °C. | −60 |
| $\Delta H_f$, Heat of Fusion[1], two weeks at 23° C., cal/g | 18.5 |
| $\Delta H_c$, Heat of Crystallization[2], cal/g | 14.6 |
| $\Delta H_f$, Heat of Fusion[3], no annealing, cal/g | 14.7 |
| $T_c$[4], (cooling rate = 10° C./min.), °C. | 20 |
| $T_c$[5], sec. | |
| at 20° C. | 0.473 |
| at 40° C. | 0.659 |
| at 80° C. | 0.533 |
| at 100° C. | 0.545 |
| at 150° C. | 0.555 |

[1]Crystalline melting point Tm and $\Delta H_f$ were determined on a sample two weeks after compression molding
[2]Heat of crystallization of molten sample cooled at 10° C./min
[3]Heat of fusion determined on the sample directly after crystallization
[4]Temperature of maximum crystallization rate after cooling at 10° C./min. from above $T_m$.
[5]Samples were heated to 100° C., cooled at 160° C./min. to designated temperature, time to reach maximum crystallization Tc was determined.

Preparation of Dental Post Pattern

The preparation of the dental post pattern comprises the following steps.

Sizing of Dental Post Blank

The apical shaft of the dental post blank is inserted into the previously prepared apical canal of the tooth. The bevel should be just above the canal opening. If necessary, the apical shaft can be cut with sharp scissors or orthodontic cutters such that the bevel is properly placed.

Apical Canal Lubrication

The apical canal is optionally, but preferably, lubricated with petroleum jelly. This is readily accomplished by placing petroleum jelly on a perio probe and pressing into the apical canal. It is most preferred that the petroleum jelly be blown to a thin layer with an air/water syringe prior to proceeding.

Application of Thermoplastic

It is most preferred that the thermoplastic be applied to the apical shaft of the dental post blank although direct insertion into the apical canal is considered within the metes and bounds of the present invention. The thermoplastic is most easily used as a stick. The end of the thermoplastic stick is heated to form a viscous polymer with a flame, hot water, a hot air blower or a similar means. A viscous polymer is defined as a polymer which is at a sufficiently high temperature to be easily molded but not so high as to cause free flow as in a liquid. The apical shaft of the dental post blank and the viscous polymer are brought into contact which causes the polymer to stick to the apical shaft. The dental post blank is then simultaneously pulled away from the thermoplastic stick and rotated on its axis thereby wrapping the viscous thermoplastic around the apical shaft of the dental post blank encasing the apical shaft. The thermoplastic stick can be separated from the viscous thermoplastic by rapidly separating the two pieces or by clipping. It may be desirable to smooth the viscous thermoplastic prior to insertion into the apical canal. This can be accomplished by simply placing a small layer of petroleum jelly on the thumb and forefinger and gently forming the viscous thermoplastic in the shape of a cone.

Insertion Into Apical Canal

The apical shaft of the dental post blank coated with viscous thermoplastic is pressed into the apical canal to the desired depth. Excess viscous thermoplastic should be displaced to form a bead as previously described. Once seated, it may be beneficial to lift and reseat to insure the pattern does not include any undercut regions in the tooth which would inhibit subsequent removal of the pattern. The thermoplastic is allowed to cool while still in the apical canal thereby maintaining the pattern of the apical canal.

After the pattern is complete one of three procedures may follow. A final impression may be formed on the transfer head; the transfer head may be altered or removed and a core pattern prepared; or a temporary crown may be prepared on the transfer head. A temporary crown is not recommended for long term use since fracture of the transfer head is possible.

A final impression of the reconstructed tooth can be prepared directly on the transfer head, as typically done on a core, or a temporary crown may be prepared on the transfer head. The final impression, and frozen thermoplastic pattern of the apical canal are then used in the cast process in a conventional manner. The cast process comprises the steps of forming a cast pattern followed by molding a replicate of the thermoplastic pattern and reconstructed tooth.

The preferred embodiments are set forth to describe the present invention and the most expected manner of use. The preferred embodiments are not intended to limit the scope of the invention. It would be apparent that other modifications and uses of the invention will be apparent to a skilled artisan which would not depart from the spirit of the invention.

I claim:

1. An apparatus for forming a removable pattern of an apical canal comprising:
   an elongated apical shaft;
   a transfer head axially attached to one end of said apical shaft;
   a thermoplastic encasing said apical shaft wherein said thermoplastic, said transfer head and said elongated apical shaft are suitable for forming a removable pattern of said apical canal.

2. The apparatus for forming a removable pattern of an apical canal of claim 1 wherein said thermoplastic has a melting point of about 120° F. to about 160° F.

3. The apparatus for forming a removable pattern of an apical canal of claim 2 wherein said thermoplastic is crystalline below about 105° F.

4. The apparatus for forming a removable pattern of an apical canal of claim 2 wherein said thermoplastic comprises a caprolactone defined by the formula:

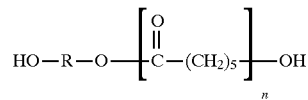

wherein R is an aliphatic hydrocarbon of 1 to about 25 carbons and n is an integer of 300 to 650.

5. The apparatus for forming a removable pattern of an apical canal of claim 1 further comprising a bevel between said transfer head and said apical shaft.

6. The apparatus for forming a removable pattern of an apical canal of claim 1 wherein said apical shaft comprises at least one taper.

7. The apparatus for forming a removable pattern of an apical canal of claim 1 wherein said transfer head is rotationally asymmetrical.

8. The apparatus for forming a removable pattern of an apical canal of claim 7 wherein said transfer head comprises a shape chosen from a semi-circle or trapezoid or said transfer head comprises a slot, groove or rib.

9. The apparatus for forming a removable pattern of an apical canal of claim 1 further comprising a superstructure attached to said transfer head.

10. A process for forming a cast post dental restoration pattern comprising the steps of:
   (a) inserting a dental post blank into the apical canal wherein said dental post blank comprises:
      (i) an elongated apical shaft;
      (ii) a transfer head axially attached to said apical shaft;
      (iii) a viscous thermoplastic encasing said apical shaft;
   (b) allowing said viscous thermoplastic to harden thereby forming a removable, rigid impression of said apical canal rigidly attached to said apical shaft; and
   (c) removing said dental post blank and said rigid impression of said apical canal.

11. The process for forming a cast post dental restoration pattern of claim 10 further comprising the step of constructing a dental restoration pattern on said transfer head.

12. The process for forming a cast post dental restoration pattern of claim 10 further comprising the step of forming a core.

13. The process for forming a cast post dental restoration pattern of claim 10 further comprising the step of replicating said cast post restoration pattern by forming a cast and molding a replicate.

14. The process for forming a cast post dental restoration pattern of claim 10 wherein said thermoplastic is 120° F. to 160° F.

15. The process for forming a cast post dental restoration pattern of claim 10 wherein said thermoplastic comprises

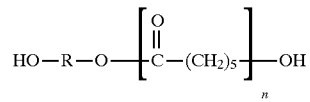

wherein R is an aliphatic hydrocarbon of 1 to about 25 carbons and n is an integer of 300 to 650.

16. The process for forming a cast post dental restoration pattern of claim 10 wherein said transfer head is rotationally asymmetrical.

17. The process for forming a cast post dental restoration pattern of claim 10 wherein said dental post blank further comprises a bevel.

* * * * *